United States Patent [19]

Darsow et al.

[11] Patent Number: 5,696,303

[45] Date of Patent: Dec. 9, 1997

[54] PROCESS FOR THE PREPARATION OF ALIPHATIC α, ω-DIOLS

[75] Inventors: Gerhard Darsow, Krefeld; Gerd-Michael Petruck, Erkrath; Heinz-Jürgen Alpers, Krefeld, all of Germany

[73] Assignee: Bayer Aktiengesellschaft, Leverkusen, Germany

[21] Appl. No.: 583,346

[22] Filed: Jan. 5, 1996

[30] Foreign Application Priority Data

Jan. 13, 1995 [DE] Germany ............ 195 00 783.2

[51] Int. Cl.$^6$ .................................................. C07C 29/14
[52] U.S. Cl. ................................... 568/864; 568/852
[58] Field of Search ................................ 568/864, 852

[56] References Cited

FOREIGN PATENT DOCUMENTS

| | | |
|---|---|---|
| 1023750 | 2/1958 | Germany . |
| 2321101 | 11/1974 | Germany . |
| 2605107 | 8/1977 | Germany . |
| 1300889 | 12/1972 | United Kingdom . |
| 1534232 | 11/1978 | United Kingdom . |
| 8203854 | 11/1982 | WIPO . |

OTHER PUBLICATIONS

Chemical Abstracts, vol. 82, abstract No. 86070a, abstract of DE 2,321,101, p. 495, (1975).

Chemical Abstracts , #5477i; abstract of DE1023750; Thelen et al., 1960.

*Primary Examiner*—C. Warren Ivy
*Assistant Examiner*—S. Padmanabhan
*Attorney, Agent, or Firm*—Sprung Kramer Schaefer & Briscoe

[57] ABSTRACT

In a process for the preparation of aliphatic α,ω-diols of 4 to 12 carbon atoms from aliphatic α,ω-dicarboxylic acids of 4 to 12 carbon atoms, an oligo ester is first of all formed from diol and dicarboxylic acid and is subsequently subjected to catalytic hydrogenation in the liquid phase. The hydrogenation is carried out continuously at from 180° to 250° C. and at an $H_2$ pressure of from 100 to 400 bar over a catalyst in piece form comprising compressed powders of Cu, Zn and Al oxides which do or do not contain at least one oxide of metals of the iron group of the Periodic Table of the Elements (Mendeleev) or of manganese. The quantity of $H_2$ is from 20 to 100 times the stoichiometrically required quantity.

20 Claims, No Drawings

PROCESS FOR THE PREPARATION OF ALIPHATIC α, ω-DIOLS

BACKGROUND OF THE INVENTION

1. Field of the Invention

The present invention relates to a process for the preparation of aliphatic α,ω-diols of 4 to 12 carbon atoms from aliphatic α,ω-dicarboxylic acids of 4 to 12 carbon atoms, in which only very small quantifies are formed of the monoalcohols of carbon numbers 1 to 12 which are customarily produced as by-products in the hydrogenation of such acids or their ester derivatives, and in which no $C_4$–$C_{12}$ lactones and no $C_4$–$C_{12}$ ω-hydroxycarboxylic acids are formed. To this end, the use of monoalcohols for the ester preparation is avoided by first of all preparing an oligomeric diol dicarboxylate from the carboxylic acid to be employed and from the diol to be prepared, which dicarboxylate is subsequently hydrogenated catalytically in the liquid phase with hydrogen, without being purified further by distillation. The conditions mentioned render the process according to the invention ecologically and industrially advantageous.

Aliphatic α,ω-diols, for example hexane-1,6-diol, are important monomers for the production of thermoplastic polyesters and of polyurethanes having particular mechanical and chemical properties. For this purpose, such diols can be employed in pure form or as mixtures of two or more diols having different chain lengths within the $C_4$–$C_{12}$ range.

2. Description of the Related Art

To prepare hexane-1,6-diol, for example, it is known to hydrogenate adipic acid or its salts directly, in aqueous solution or in an organic solvent, by a batchwise (DE-A-26 05 107; GB 1,300,889) or continuous (DE-A-23 21 101) procedure in which, alongside hexane-1,6-diol, relatively large proportions of caprolactone, ω-hydroxy-caproic acid and monoalcohols with carbon numbers from 1 to 6 are always formed. For the same purpose, it is also known to esterify adipic acid with monoalcohols, to give a di-n-alkyl adipate which is hydrogenated in the gas phase to give hexane-1,6-diol (WO 82/03854). It is also known to esterify adipic acid with diols, such as hexane-1,6-diol, by a batchwise procedure to give a mixture of higher esters, which is hydrogenated in a batchwise autoclave process to give hexane-1,6-diol and ω-hydroxy-caproic esters, the hydrogenation catalyst employed being a pulverulent copper chromite catalyst (DE-B-10 23 750).

SUMMARY OF THE INVENTION

The invention relates to a process for the preparation of aliphatic α,ω-diols of 4 to 12 carbon atoms from aliphatic α,ω-dicarboxylic acids of 4 to 12 carbon atoms by oligoesterification of the said dicarboxylic acids with the said diols and catalytic hydrogenation of the resulting oligo ester in the liquid phase, which is characterized in that the oligo ester is hydrogenated continuously at from 180° to 250° C., preferably from 190° to 240° C., and at an $H_2$ pressure of from 100 to 400 bar, preferably from 150 to 300 bar, the quantity of $H_2$ being from 20 to 100 times the stoichiometrically required quantity, over a catalyst in piece form consisting of compressed powders of Cu oxides, Zn oxides and Al oxides which do or do not contain at least one oxide of metals of the iron group of the Periodic Table of the Elements (Mendeleev) or of manganese.

DETAILED DESCRIPTION OF THE INVENTION

The course of the reaction can be illustrated, based on the formation of hexane-1,6-diol from adipic acid using hexane-1,6-diol for the oligoesterification, by the following set of equations:

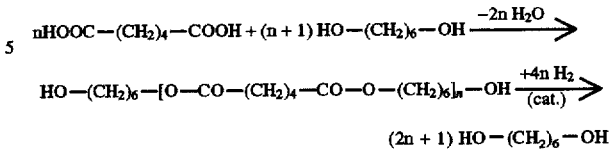

$$(2n + 1) HO-(CH_2)_6-OH$$

In the processes which have been disclosed to date, relatively large quantities of by-products are always obtained, which give rise to considerable complexity in the preparation of the reaction product in pure form. Recycling is not always possible, since the hydrogenation does not always, as already mentioned above, proceed smoothly to the desired product, and would therefore lead to a higher level of circulated by-products. Another fundamental difficulty is the monoalcohol which has so far been employed for esterification, which must in principle be separated from the end product. The fixation with monoalcohols for the esterification is very obviously explained by the fact that, in the course of development of the hydrogenation process from the liquid to the gaseous phase, it was necessary to have available an ester which could be evaporated easily. A further argument in favour of such readily evaporable esters from monoalcohols is the fact that they can openly be prepared in pure form; this appeared to be very important, since contaminated starting materials in hydrogenations generally lead to difficulties. Such esters of dicarboxylic acids and lower alcohols, for example methanol, ethanol or propanol, however, generally require the use of an esterification catalyst and a water entrainer such as, for example, toluene, both of which substances are alien to the system and must be separated off. The use of a water entrainer which must be distilled off from the reaction mixture as an azeotropic mixture with the water of reaction formed, separated from the water and recycled to the reaction mixture constitutes an additional expense in terms of apparatus. Furthermore, a relatively large quantity of energy has to be employed in order to distil off the entrainer, whose quantity constitutes a multiple of the quantity of water formed, repeatedly from the reaction mixture. Finally, the dialkyl dicarboxylate must be carefully freed from esterification catalyst prior to the catalytic hydrogenation, by distillation or other laborious purification measures. Following hydrogenation, the monoalcohol has to be separated from the reaction products, which involves technical effort, worked up to the pure alcohol and returned to the esterification process, with unavoidable losses of alcohol having to be made up.

If it is desired to esterify a dicarboxylic acid with higher-boiling alcohols, for example those having carbon numbers of more than 3, in order to hydrogenate them as dialkyl esters in the gas phase, it might be possible to dispense with the esterification catalyst and the entrainer, but one would then require in addition, as a substance alien to the reaction, the relatively expensive, higher-boiling monoalcohol, which must likewise be Worked up to the pure alcohol again and returned to the esterification process, in which case unavoidable losses of alcohol have to be made up here as well; owing to the relatively high price of such alcohols, these losses severely affect the economy of such a process. Because of the higher boiling points, in addition, a greater mount is expended for each distillation.

The situation is different and advantageous if, in order to esterify the dicarboxylic acid of 4 to 12 carbon atoms, a diol of 4 to 12 carbon atoms is employed, since in such a case neither esterification catalysts nor entrainers are required and since the esterifying diol can, as a substance inherent in the system, remain in the reaction product. For the intended uses mentioned above it is permissible in many cases to employ a mixture of diols of different chain lengths; therefore it is not necessary to employ a diol having the same number of carbon atoms in the oligoesterification of the dicarboxylic acid. Rather, in accordance with the invention it is permissible, for example, to react adipic acid not only with hexane-1,6-diol but also with butane-1,4-diol, octane-1,8-diol and other diols and then to obtain a mixture of, for example, $C_6$ diol with $C_4$ diol or with $C_8$ diol. In order, however, to obtain α,ω-diols as reaction products with a uniform carbon number, the dicarboxylic acid to be reacted is oligoesterified with a diol of the same carbon number and hydrogenated, for example adipic acid with hexane-1,6-diol, succinic acid with butane-1,4-diol, suberic acid with octane-1,8-diol, etc.

Examples of dicarboxylic acids which can be employed in accordance with the invention, having even or odd numbers of carbon atoms including in each case the carbon atoms of the two carboxyl groups, are: succinic acid, glutaric acid, adipic acid, pimelic acid, suberic acid, heptanedicarboxylic acid, octanedicarboxylic acid and decanedicarboxylic acid. These acids are known and are obtainable from natural or synthetic sources.

Examples of α,ω-diols having even or odd numbers of carbon atoms, which are to be prepared in accordance with the invention and can be employed in the oligoesterification step, are butane-1,4-diol, pentane-1,5-diol, hexane-1,6-diol, heptane-1,7-diol, octane-1,8-diol, decane-1,10-diol and dodecane-1,12-diol.

The process according to the invention is particularly important for the preparation of hexane-1,6-diol by oligoesterification of adipic acid with hexane-1,6-diol and subsequent hydrogenation.

In order to prepare oligo esters as required in the process according to the invention, for example to prepare hexane-1,6-diol adipate, a discontinuous process (batch process) is normally employed, in which the dicarboxylic acid ,and the diol are esterified in a reactor with or without catalyst and the water formed during the esterification is removed from the reaction mixture with or without an entrainer. Such oligo esters can be employed in accordance with the invention. Batch processes of the type described, however, have the disadvantage that their capacity is small relative to the reaction volume and there is therefore a need for large reactors and storage tanks. The energy consumption is uneconomic and the personnel requirements are relatively high.

Continuous esterification processes with a plurality of esterification reactors in a cascade avoid some of these disadvantages. Therefore, a preferred variant of the process according to the invention is that the oligoesterification is carried out not only in the batchwise procedure but also in a quasi-continuous procedure, and therefore, apart from in only one esterification stage, also in up to four esterification stages, preferably quasi-continuously in two or three esterification stages with distillative removal of the water of reaction. Suitable ranges in this context are from 100° to 240° C. for the temperature and from 1500 to 100 mbar for the pressure. Even this procedure in more than one, preferably 2 to 4 esterification stages, preferably 2 or 3 esterification stages, is barely able alone to bring about any substantial reduction in the relatively long reaction times of, for example, 12 hours or more, unless the discharge of water from the reaction mixture is accelerated by technical measures, for example by high-speed stirrer systems. A further acceleration in the discharge water is, for example, that achieved by blowing in a propellant gas, for example by blowing in nitrogen.

In contrast, it is significantly more effective, and therefore represents a further preferred variant of the process according to the invention, to combine a reactor cascade with a temperature cascade. Thus it has proved to be useful to start the esterification reaction of the liquid-melt starting components initially at a relatively low reaction temperature of, for example, from 110° to 150° C., in order to continue this reaction in a second and subsequent esterification stage at elevated temperature, the temperature being increased from stage to stage by from 10° to 40° C., preferably by from 15° to 30° C. Within each stage the temperature can not only vary slightly but can also be increased deliberately by from 5° to 30° C. In addition to the temperature cascade, it is also possible for the pressure to be altered, in which context, in the general range from 1500 to 100 mbar, an increase in temperature entails in principle reduction in pressure. Thus, for example, in the case of a multistage oligoesterification the first stage can be carried out at atmospheric pressure, the last stage at from 200 to 600 mbar and; in the case of 3 or 4 stages, the middle stage(s) at from 400 to 100 mbar.

In a single-stage procedure, and likewise when using a plurality of reactors, the oligoesterification can be carried out such that, in a certain time cycle, the reactors are filled with esterification mixture at different points in time. Thus a new batch of oligo ester for the subsequent hydrogenation is in each case available after a shorter time than is required for the overall esterification. In a multistage esterification in the manner described, the esterification mixture for carrying out the subsequent esterification stage is transferred from one reactor to the other. The reactor which has been emptied in each case can then be filled with a follow-on batch. In this case too, a new batch of oligo ester for the subsequent hydrogenation is available after a shorter time than is required for the overall oligoesterification. In this way, a quasi-continuous oligoesterification is possible.

The reaction apparatus suitable for the oligoesterification comprises in general one or more reactors made from acid-resistant material, which is equipped with an effective stirrer and with a mounted distillation column of conventional construction with from 8 to 15 trays.

If it is desired, for example, to esterify a dicarboxylic acid with a diol in the molar ratio of 1:1 under the esterification conditions indicated, then a mixture of oligo esters with different degrees of oligomerization (=number of molecules of dicarboxylic acid in the oligo ester) is obtained whose molecular mass distribution follows very closely a bell curve. The average degree of oligomerization n in the sense of the above set of equations is n=9, the acid number being above 50 mg of KOH/g of reaction product. In order to obtain lower acid numbers, and thus substantially to suppress instances of corrosion, and in addition to move the average chain length of the oligo ester towards shorter chain lengths, it is expedient to carry out esterification in the presence of a molar excess of diol. If the dicarboxylic acid is then esterified with a diol in the molar ratio of 1:2 under the reaction conditions indicated, then it is indeed certain that the free carboxyl groups are esterified relatively quickly and the oligo ester mixture obtained only has an average chain length of, for example, n=5, but it is necessary to employ a relatively high proportion of diol. Surprisingly it has now been found—and this constitutes a further advantageous variant of the process according to the invention— that, even with a slight molar excess of diol based on the dicarboxylic acid, acid numbers of not more than 50 mg of KOH/g of reaction mixture can be achieved, for example acid numbers of from 20 to 50. A molar ratio of this kind for the oligo ester required makes up from 1.03 to 1.15 mol, preferably from 1.05 to 1.12 mol, of diol per mole of the dicarboxylic acid. The average degrees of esterification (degrees of oligomerization) obtained in this case vary within the range from n=3 to n=6.

The dicarboxylic acids employed and the diols employed normally have a purity of more than 99%. Because of the fact that substances alien to the system can be dispensed with, however, the purity of distillation recyclates from the hydrogenation step which follows the oligoesterification is also entirely adequate for carrying out the process according to the invention, even if these distillation recyclates contains small quantities of unhydrogenated oligo ester. Such recycled oligo esters and other components must be taken into account when establishing the stated molar ratio of diol to dicarboxylic acid.

A further advantage of the process according to the invention is that the oligo ester thus prepared can be processed further directly in the hydrogenated stage without additional purification steps.

The hydrogenation step in the process according to the invention is carried out in the liquid phase with excess hydrogen which makes up from 20 to 100 times the stoichiometrically required quantity. By working in the liquid phase, the energy consumption involved in gas-phase processes is reduced, thus bringing cost savings. While a discontinuous process (batch process) is still widely employed for the hydrogenation of esters, such a process likewise being subject to the disadvantages set out for the esterification, and such a process employing pulverulent catalysts in a suspension technique, the process according to the invention is operated with complete continuity in its hydrogenation stage. In addition, the hydrogenation stage is carried out over a catalyst in piece form. The difficulties involved with pulverulent catalysts are hereby circumvented, namely the difficulty of activating powder catalysts in a specific and uniform manner, the difficulty of circulating powder catalysts with the aid of special suspension pumps, and the difficulty of achieving quantitative separation of powder catalysts from the reaction product. Indeed, suspension pumps are subject to high mechanical stresses. The quantitative removal of pulverulent catalysts, furthermore, is complex since it requires a coarse filtration and a fine filtration with apparatus in changeover design. In addition, there is a great risk of the catalysts rapidly losing their activity as a result of these additional operations, meaning that high catalyst consumption figures must still be expected. In contrast to these difficulties which have been indicated, the piece-form catalysts to be employed in accordance with the invention possess a high insensitivity to acid, high insensitivity to pressure and have a high activity, which does not drop off even over a period of one or more years. The latter advantage is very important, since frequent catalyst changeover is very laborious even with catalysts in piece form arranged in a fixed bed.

The piece-form catalyst to be employed in accordance with the invention consists of compressed powders of Cu oxides, Zn oxides and Al oxides in which the Cu proportion is from 40 to 60% by weight, the Zn proportion is from 15 to 30% by weight and the Al proportion is from 0.2 to 6% by weight, all figures being based on the total quantity of the oxide powder mixture, and the remainder to 100% by weight constituting oxygen. Such a catalyst can be employed in this form without further additions for the hydrogenation step according to the invention. Advantageously, however, it additionally includes a content of at least one oxide of metals from the iron group of the Period Table of the Elements (Mendeleev) and/or of manganese. Suitable elements from the iron group in this context are iron, cobalt and nickel. Oxides of the elements iron, cobalt, nickel and manganese, preferably iron, cobalt and nickel, can be employed both individually and in a mixture of oxides of a plurality of the elements mentioned. The total quantity of oxides from the iron group and/or of manganese in the compressed oxide powder is from 0.05 to 1.5% by weight, preferably from 0.1 to 0.5% by weight, of the total oxide powder for the hydrogenation catalysts. Where a plurality of oxides of elements from the iron group and of manganese are employed, each of these mixed oxides is present in a quantity which is not less than 20% and not more than 80% of the abovementioned total range of from 0.05 to 1.5% by weight.

The catalysts to be employed should as far as possible be free from alkali metals and alkaline earth metals; the maximum permissible contamination level in this case is 0.1% by weight, based on the total quantity of the oxide powder mixture.

The carrier-free catalyst in piece form can be prepared by conventional methods by compressing the metal-oxide powders, for example on tabletting or pelletizing machines, under a high pressure, in which context it is also possible, in order to improve the adhesion capacity of the metal oxide particles, to use graphite and/or adhesives in quantities of from 0.5 to 3% by weight, based on the total weight of the constituents to be compressed. Examples of the piece form of the catalysts are tablets, balls or granules with dimensions of from 2 to 10 mm, preferably from 3 to 7 mm. In order to enlarge the external surface area, it is also possible for tabletted forms to be provided with an axial through bore. Such forms, if viewed macroscopically, have a smooth surface. In order to achieve a long service life (lifetime), the catalysts in piece form must have a compressive strength of from 50 to 200N, preferably from 75 to 150N, on the surface of the shaped form. The catalysts in piece form additionally have an internal surface area of from 10 to 90 $m^2/g$, preferably from 30 to 80 $m^2/g$. The compressive strength of the carrier-free catalyst in piece form can be determined in accordance with DIN 50 106. The internal surface areas are determined according to Analyt. Chem. 30 (1958), pages 1387–1390 or according to S. J. Gregg and S. W. Sing, Adsorption, Surface Area and Porosity, London 1982, Chap. 2 and 6.

The shaped forms employed as hydrogenation catalysts, comprising compressed powders of Cu oxides, Zn oxides and Al oxides with or without a content of at least one oxide of metals from the iron group or of manganese, must be carefully reduced before being employed. This is effected by treatment with hydrogen at from 180° to 200° C., employing at the beginning of the treatment a mixture of from 10 to 15% by volume of $H_2$ and from 90 to 85% by volume of inert gas (e.g. nitrogen) and, in the course of the treatment, reducing the inert gas component down to zero % by volume. Such a treatment is carried out over a period of from about 15 to 30 hours and is complete when the catalyst no longer consumes hydrogen and, consequently, no longer forms water of reaction.

The hydrogenation step in the process according to the invention is carried out continuously in the liquid phase at from 180° to 250° C., preferably from 190° to 240° C., and at an $H_2$ pressure of from 100 to 400 bar, preferably-from 150 to 300 bar, using pure hydrogen.

While it is in principle equivalent to let the oligo ester mixture to be hydrogenated flow from the bottom to the top or from the top to the bottom in the hydrogenation reactor, it has been found advantageous to let the oligo ester mixture flow from the top to the bottom over the catalyst (trickle phase). In this context, the oligo ester mixture to be hydrogenated can either flow over the catalyst together with the hydrogen, introduced separately or mixed in beforehand (co-current technique) or can alternatively be led against the hydrogen (countercurrent technique).

The hydrogenation reactor can on the one hand be a single high-pressure pipe made of steel or a steel alloy, which is filled completely or partly with the catalyst in piece form, in which case, with relatively large pipe cross-sections, it may also be useful to deploy the carrier-free catalysts in piece form on trays (wire baskets or the like); however, it is also possible to use bundles of high-pressure pipes within a common housing, the individual pipes in turn being filled completely or partially with the carrier-free catalysts in piece form.

The hourly space velocity can be from 200 to 600 ml of oligo ester mixture per liter of catalyst. Under the reaction conditions specified, high catalyst service lives of from 8000 to 16,000 hours can be achieved. The reaction mixture leaving the hydrogenation reactor, after let down in which the excess hydrogen is intercepted and can be reused after it has been compressed and the consumed hydrogen has been made up, consists to the extent of more than 98.5% by weight of the anticipated diol or the anticipated mixture of diols. With regard to organic low-boiling components, it contains not more than 0.5% by weight of monoalcohols, and, with regard to high-boiling components, not more than 0.5% by weight of a residue of relatively high molecular weight. The relatively high-boiling components essentially constitute unreacted oligo ester mixture and can be recycled to the process, so that its total selectivity for the diols is at least 99.0% by weight. The diol produced is obtained, after distillative removal ,of low- and high-boiling components, in a purity of at least 99.9% by weight, in which purity it can be employed for all subsequent chemical processing operations.

EXAMPLES

Example 1

A hot solution at 110° C. of 730.7 g (5 mol) of adipic acid in 650 g (5.5 mol) if hexane-1,6-diol was placed into the first reactor of a reactor cascade comprising acid-resistant material, which consisted of three series-connected reactors having a volume of 5 l each and each fitted with a rapid stirring system of customary construction (turbine stirrer, rotary speed: from 800 to 1200/min) and a distillation column (10 theoretical plates), the solution was quickly heated with stirring to a reaction temperature of from 140° to 150° C., and the water of reaction which formed was distilled off under atmospheric pressure. After a residence time of 1.5 hours, the reaction mixture was transferred to the adjacent second reactor, in which a further portion of the water of reaction was distilled off under atmospheric pressure with stirring at a reaction temperature of from 150° to 180° C. Finally, after a further residence time of 1.5 hours, the reaction mixture was transferred to the adjacent third reactor, where the remainder of the water of reaction was removed under a pressure of 400 mbar and at a reaction temperature of from 180° to 190° C. After a residence time of 1.5 hours more (4.5 hours in all), the desired degree of esterification had been reached. The oligomeric hexane-1,6-diol adipate obtained (1,290 g) had an average degree of oligoesterification (=number of molecules of adipic acid in the oligo ester) of n=4 (measured by gel permeability chromatography) and an acid number of 25 mg of KOH/g of reaction mixture. After partial or complete emptying of the first reactor, it was possible to continue the esterification process in a quasi-continuous manner by adding new quantities of reaction mixture.

Example 2

A solution of 730.7 g (5 mol) of adipic acid in 620.5 g (5.25 mol) of, hexane-1,6-diol was placed in the first reactor of the same reactor cascade as in Example 1, the solution was heated with stirring to a reaction temperature of from 140° to 150° C., and the water of reaction which formed was distilled off under atmospheric pressure. After a residence time of 1 hour, the reaction mixture was run into the adjacent second reactor, where a further portion of the water of reaction was distilled off under atmospheric pressure at a reaction temperature of from 140° to 180° C. Finally, after a residence time of 1 hour, the reaction mixture was run into the third reactor and the remainder of the water of reaction was removed under a pressure of 350 mbar and at a reaction temperature of 180° C. After a reaction time of 2 hours more (4 hours in all), the desired degree of esterification had been reached. The oligomeric hexane-1,6-diol adipate obtained (1,256 g) had an average degree of oligoesterification of n=5 (molecular mass distribution measured by gel permeability chromatography) and an acid number of 32 mg of KOH/g of reaction mixture. Following the partial or complete emptying of the first and/or second reactor, it was possible to continue the esterification process in a quasi-continuous manner by adding new quantities of reaction mixture.

Example 3

A vertical, heat-insulated high-pressure tube made from non-corroding, acid-resistant material and with an internal diameter of 45 mm and a length of 1 m, which had been flushed beforehand with nitrogen to render it free of oxygen, was filled with 1.4 l of a hydrogenation catalyst prepared by tabletting powders of oxides of copper, zinc, aluminium and iron. The copper content of the tablets was 42% by weight, the zinc content 17% by weight, the aluminium content 2.0% by weight and the iron content 0.2% by weight. At a cylindrical height of 5 mm and a diameter of 5 mm, the tablets had a compressive strength of 125N on the cylinder outer surface and an internal surface area of 68 m$^2$/g.

In order to activate the catalyst comprising a mixture of metal oxides, the tablets were initially dried for 6 hours in a stream of nitrogen (temperature: max. 200° C., quantity: 5 m$^3$ of $N_2$/h (s.t.p.). The actual activation took place at a nitrogen pressure of 200 bar and a temperature of between 180° and 200° C., during which hydrogen was gradually mixed in with the inert gas; the proportion of this hydrogen mixed in in the initial phase must not exceed from 10 to 15% by volume. Over the course of 24 hours, the proportion of nitrogen in the gas mixture was reduced more and more until, finally, pure hydrogen flowed through the reactor. The reaction had ended when water of reaction, which was collected in a downstream separator, was no longer formed.

Following the activation of the hydrogenation catalyst, the hydrogen pressure in the reactor system was raised to 300 bar. Subsequently, per hour, 420 g of hexane-1,6-diol adipate which had been obtained according to Example 1, together with 5 m$^3$ (s.t.p.) of hydrogen at a pressure of 300 bar were pumped through the high-pressure tube, the hexane-1,6-diol adipate being heated in an upstream, electrically heated heat exchanger to a temperature of 210° C. before entry into the high-pressure tube.

The reaction product leaving the reaction tube (crude hexane-1,6-diol) was cooled in a second heat exchanger (water condenser) at 300 bar hydrogen pressure to a temperature <60° C. and separated in a gas separator from the excess hydrogen, which was returned to the hydrogenation system. After further cooling to a temperature <30° C. and depressurization to atmospheric pressure, the reaction product was analysed by gas chromatography. In terms of organic low-boiling components it contained only 0.4% by weight of monoalcohols of carbon numbers 1 to 6 and, in terms of relatively high-boiling components, 0.3% by weight of unreacted hexane-1,6-diol adipate, so that the hexane-1,6-diol content of the organic reaction product was 99.3% by weight. The hexane-1,6-diol produced was obtained, following the distillative removal of low- and high-boiling components, in a purity of ≧99.9% by weight. Since the relatively high-boiling components were returned to the process, the overall selectivity thereof with respect to hexane-1,6-diol was 99.6% by weight.

The catalyst showed unaltered activity after a service period of 7800 hours, so that the composition of the reaction product did not change over this period.

Example 4

A high-pressure tube as in Example 3 was filled under inert gas with 1.4 l of a hydrogenation catalyst produced by tabletting powders of oxides of copper, zinc, aluminium and nickel. The copper content of the tablets was 51% by weight, the zinc content 19% by weight, the aluminium content 0.5% by weight and the nickel content 0.15% by weight. At a cylinder height of 3 mm and a diameter of 3 mm, the tablets had a compressive strength of 81N on the cylinder outer surface and an internal surface area of 58 $m^2/g$.

Following the activation of the hydrogenation catalyst containing a mixture of metal oxides, as in Example 3, the hydrogen pressure was raised to 300 bar. Subsequently, per hour, 420 g of hexane-1,6-diol adipate obtained according to Example 2, together with 5 $Nm^3$ (s.t.p.) of hydrogen were pumped continuously through the high-pressure tube under a pressure of 300 bar, the hexane-1,6-diol adipate being heated to a temperature of 220° C. before entry into the high-pressure tube.

The reaction product leaving the reaction tube (crude hexane-1,6-diol), following separation from excess hydrogen and cooling to a temperature <30° C., and according to analysis by gas chromatography, contained—in terms of organic low-boiling components—0.48% by weight of monoalcohols of carbon numbers 1 to 6 and—in terms of relatively high-boiling components—0.35% by weight of unreacted hexane-1,6-diol adipate, so that the hexane-1,6-diol content of the organic reaction product was 99.17% by weight. Following the distillative removal of low- and high-boiling components, the hexane-1,6-diol produced was obtained in a purity of 99.9% by weight. Since the relatively high-boiling components were returned to the process, the overall selectivity thereof with respect to hexane-1,6-diol was 99.52% by weight.

The catalyst showed unchanged activity after a service time of 5400 hours, so that the composition of the reaction product did not change over this period.

Example 5

A high-pressure tube as in Example 3 was filled under inert gas with 1.4 l of a hydrogenation catalyst produced by tabletting powders of oxides of copper, zinc, aluminium and cobalt. The copper content of the tablets was 49% by weight, the zinc content 27% by weight, the aluminium content 1.8% by weight and the cobalt content 0.22% by weight. At a cylinder height of 5 mm and a diameter of 5 mm, the tablets had a compressive strength of 110N on the cylinder outer surface and an internal surface area of 47 $m^2/g$.

Following the activation of the oxidic hydrogenation catalyst as in Example 3, the hydrogen pressure was raised to 250 bar. Subsequently, per hour, 420 g of hexane-1,6-diol adipate obtained according to Example 2, together with 5 $Nm^3$ (s.t.p.) of hydrogen were pumped continuously through the high-pressure tube under a pressure of 250 bar, the hexane-1,6-diol adipate being heated to a temperature of 220° C. before entry into the high-pressure tube. The crude product leaving the reaction tube (crude hexane-1,6-diol), following separation of excess hydrogen and cooling to a temperature <30° C., and according to analysis by gas chromatography, contained—in terms of organic low-boiling components—0.68% by weight of monoalcohols of carbon numbers 1 to 6 and—in terms of relatively high-boiling components—0.38% by weight of unreacted hexane-1,6-diol adipate, so that the hexane-1,6-diol content of the organic reaction product was 98.94% by weight. Since the unreacted hexane-1,6-diol adipate was returned to the process, the overall selectivity thereof with respect to hexane-1,6-diol was 99.32% by weight.

The catalyst showed unchanged activity after a service period of 3800 hours, so that the composition of the reaction product was unchanged over this period.

Example 6

A solution of 590.5 g (5 mol) of succinic acid in 504.7 g (5.6 mol) of 1,4-butanediol was placed in the first reactor of the same reactor cascade as in Example 1, the solution was heated with stirring to a reaction temperature of 130°–140° C., and the water of reaction which formed was distilled off under atmospheric pressure. After a residence time of 2 hours, the reaction mixture was run into the adjacent second reactor, where a further portion of the water of reaction was distilled off under atmospheric pressure at a reaction temperature of 140°–160° C. Finally, after a residence time of 1 hour, the reaction mixture was run into the third reactor and the remainder of the water of reaction was removed under a pressure of 800 mbar and at a reaction temperature of 160° C. After a reaction time of 2 hours more (5 hours in all), the desired degree of esterification had been reached. The oligomeric butane-1,4-diol succinate obtained (1,005 g) had an average degree of oligoesterification of n=5 (molecular mass distribution measured by gel permeability chromatography) and an acid number of 46 mg of KOH/g of reaction mixture. Following the partial or complete emptying of the first and/or second reactor, it was possible to continue the esterification process continuously by adding new quantifies of reaction mixture.

Example 7

A vertical, heat-insulated high-pressure tube made from non-corroding, acid-resistant material and with an internal diameter of 45 mm and a length of 1 m, which had been flushed beforehand with nitrogen to render it free of oxygen, was filled with 1.4 l of a hydrogenation catalyst prepared by tabletting powders of oxides of copper, zinc, aluminium and iron. The copper content of the tablets was 42% by weight, the zinc content 17% by weight, the aluminium content 2.0% by weight and the iron content 0.2% by weight. At a cylindrical height of 5 mm and a diameter of 5 mm, the tablets had a compressive strength of 125N on the cylinder outer surface and an internal surface area of 68 m²/g.

In order to activate the catalyst comprising a mixture of metal oxides, the tablets were initially dried for 6 hours in a stream of nitrogen (temperature: max. 200° C., quantity: 5 m³ of N₂/h (s.t.p.). The actual activation took place at a nitrogen pressure of 100 bar and a temperature of between 180° and 200° C., during which hydrogen was gradually mixed in with the inert gas; the proportion of this hydrogen mixed in in the initial phase must not exceed 10–15% by volume. Over the course of 24 hours, the proportion of nitrogen in the gas mixture was reduced more and more until, finally, pure hydrogen flowed through the reactor. The reaction had ended when water of reaction, which was collected in a downstream separator, was no longer formed.

Following the activation of the hydrogenation catalyst, the hydrogen pressure in the reactor system was raised to 150 bar.

Subsequently, per hour, 420 g of butane-1,4-diol succinate which had been obtained according to Example 1, together with 5 m³ (s.t.p.) of hydrogen at a pressure of 150 bar were pumped through the high-pressure tube, the butane-1,6-diol succinate being heated in an upstream, electrically heated heat exchanger to a temperature of 210° C. before entry into the high-pressure tube.

The reaction product leaving the reaction tube (crude butane-1,4-diol) was cooled in a second heat exchanger (water condenser) at 300 bar hydrogen pressure to a temperature <60° C. and separated in a gas separator from the excess hydrogen, which was returned to the hydrogenation system.

After further cooling to a temperature <30° C. and depressurization to atmospheric pressure, the reaction product was analysed by gas chromatography.

In terms of organic low-boiling components it contained 0.2% by weight of tetrahydrofuran and 0.1% by weight of n-butanol and, in terms of relatively high-boiling components, 0.4% by weight of unreacted butane-1,4-diol succinate, so that the butane-1,4-diol content of the organic reaction product was 99.3% by weight.

The 1,4-butanediol produced was obtained, following the distillative removal of low- and high-boiling components, in a purity of ≧99.9% by weight.

Since the relatively high-boiling components were returned to the process, the overall selectivity thereof with respect to butane-1,4-diol was 99.7% by weight.

The catalyst showed unchanged activity after a service period of 5,600 hours, so that the composition of the reaction product did not change over this period.

What is claimed is:

1. A process for the preparation of an aliphatic α,ω-diol of 4 to 12 carbon atoms from an aliphatic α,ω-dicarboxylic acid of 4 to 12 carbon atoms by oligoesterification of the said dicarboxylic acids with the said diol and catalytic hydrogenation of the resulting oligo ester in the liquid phase, wherein the oligo ester is hydrogenated continuously at from 180° to 250° C. and at an H₂ pressure of from 100 to 400 bar, the quantity of H₂ being from 20 to 100 times the stoichiometrically required quantity, over a catalyst in piece form consisting of compressed powders of Cu oxides, Zn oxides and Al oxides which do or do not contain a least one oxide of metals of the iron group of the Periodic Table of the Elements (Mendeleev) or of manganese.

2. The process of claim 1, wherein the hydrogenation is carried out at 190° to 240° C.

3. The process of claim 1, wherein the H₂ pressure is from 150 to 300 bar.

4. The process of claim 1, wherein the oligoesterification is carried out batchwise or quasi-continuously in 1 to 4 esterification stages with distillative removal of the water of reaction in the temperature range from 100° to 240° C. and in the pressure range from 1500 to 100 mbar.

5. The process of claim 4, wherein the oligoesterification is carried out quasi-continuously in 2 or 3 esterification stages.

6. The process of claim 4, wherein, in the case of multistage oligoesterification, the temperature is increased from stage to stage by from 10° to 40° C. and within each stage by from 5° to 30° C.

7. The process of claim 6, wherein the temperature is increased from stage to stage by from 15° to 30° C.

8. The process of claim 4, wherein, in the case of multistage oligoesterification, the first stage is carried out at atmospheric pressure and the last stage at from 200 to 600 mbar.

9. The process of claim 4, wherein in the case of 3 or 4 stages, the middle stage(s) is(are) carried out at from 400 to 1000 mbar.

10. The process of claim 1, wherein the oligo ester employed is prepared from a mixture of from 1.03 to 1.15 mol of diol per mole of dicarboxylic acid in such a way that an average degree of esterification of from 3 to 6 and an acid number of from 20 to 50 mg of KOH/g of oligo ester is achieved.

11. The process of claim 10, wherein the mixture is from 1.05 to 1.12 mol of diol per mole of dicarboxylic acid.

12. The process of claim 1, wherein the oligo ester employed is used without further purification for hydrogenation.

13. The process of claim 1, wherein, in the mixture of the compressed oxide powders, the Cu porportion is from 40 to 60% by weight, the Zn proportion is from 15 to 305 by weight and the Al proportion is from 0.2 to 6% by weight, all figures being based on the total quantity of the oxide powder mixture, and the remainder to 100% by weight constituting oxygen.

14. The process of claim 1, wherein, in addition, one or more oxides of the iron group or of manganese are present in the compressed oxide powder, and the total quantity thereof is from 0.05 to 1.5% by Weight of the total oxide powder.

15. The process of claim 14, wherein the quantity of the oxides of the iron group or of manganese is from 0.1 to 0.5% by weight.

16. The process of claim 1, wherein the catalyst in piece form comprising compressed oxide powders has a cylindrical or spherical form with dimensions of from 2 to 10 mm and a compressive strength of from 50 to 200N on the shaped-body surface and an internal surface area of from 10 to 90 m²/g.

17. The process of claim 16, wherein the dimensions of the catalyst are from 3 to 7 mm.

18. The process of claim 16, wherein the catalyst has a compressive strength of from 75 to 150N.

19. The process of claim 16, wherein the catalyst has an internal suface area of from 30 to 80 m²/g.

20. The process of claim 1, wherein the catalyst of compressed oxide powder is activated prior to hydrogenation by treatment with H₂ from 180° to 200° C., employing at the beginning of the treatment a mixture of from 10 to 15% by volume of H₂ and from 90 to 85% by volume of inert gas and, in the course of the treatment, reducing the inert gas component down to zero % by volume.

* * * * *

UNITED STATES PATENT AND TRADEMARK OFFICE
CERTIFICATE OF CORRECTION

PATENT NO. : 5,696,303
DATED : December 9, 1997
INVENTOR(S) : Darsow, et al.

It is certified that error appears in the above-indentified patent and that said Letters Patent is hereby corrected as shown below:

Col. 12, line 35   Delete " 305 " and substitute
                   -- 30% --

Signed and Sealed this

Eighth Day of September, 1998

Attest:

BRUCE LEHMAN

Attesting Officer    Commissioner of Patents and Trademarks